US012239474B1

(12) United States Patent
Alodhayb et al.

(10) Patent No.: US 12,239,474 B1
(45) Date of Patent: Mar. 4, 2025

(54) SENSITIVE DETECTION OF LOW DOSES OF BETA PARTICLES USING QUARTZ CRYSTAL OSCILLATORS

(71) Applicant: KING SAUD UNIVERSITY, Riyadh (SA)

(72) Inventors: Abdullah Nasser Alodhayb, Riyadh (SA); Nadyah Layeh Alanazi, Riyadh (SA); Hamad Albrithen, Riyadh (SA); Saad Abdulaziz Dawood, Riyadh (SA); Muthumare Eswaran Muthu Ramamoorthy, Riyadh (SA); Khaled Zouher Shamma, Riyadh (SA); Saja Hamed Alshereef, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/767,749

(22) Filed: Jul. 9, 2024

(51) Int. Cl.
*A61B 6/03* (2006.01)
*A61B 6/42* (2024.01)
(Continued)

(52) U.S. Cl.
CPC ............ *A61B 6/4258* (2013.01); *A61B 6/037* (2013.01); *G01N 23/06* (2013.01); *G01N 27/14* (2013.01);
(Continued)

(58) Field of Classification Search
CPC ........ G01N 23/06; G01N 23/10; G01N 23/12; G01N 23/16; G01N 23/18;
(Continued)

(56) References Cited

U.S. PATENT DOCUMENTS 2,500,473 A * 3/1950 Spaeth ...................... G01T 1/16
455/92
2,617,955 A * 11/1952 Mandeville ............. H01J 47/08
313/538
(Continued)

OTHER PUBLICATIONS

Nadyah Alanazi et al., Sensitive detection of low doses beta particles using quartz crystal oscillators, Journal of Radiation Research and Applied Sciences, 17 (2024), 100921. (Year: 2024).*
(Continued)

*Primary Examiner* — Allen C. Ho
(74) *Attorney, Agent, or Firm* — Nath, Goldberg & Meyer; Joshua B. Goldberg

(57) ABSTRACT

A method of determining beta radiation intensity based on calculated resonance frequency and calculated quality factor can include providing an electrical sensor comprising at least one prong, irradiating the first composite material of the one of the plurality of planar surfaces and the material of the second section with beta radiation from a beta radiation source; measuring at least one impedance value from the electrical sensor with an impedance analyzer; calculating at least one resonance frequency value based on the measured at least one impedance value; calculating at least one quality factor value based on the calculated at least one resonance frequency value; and determining the beta radiation intensity based on the calculated at least one resonance frequency value and the calculated at least one quality factor value.

15 Claims, 14 Drawing Sheets

(51) Int. Cl.
*G01N 23/06* (2018.01)
*G01N 27/14* (2006.01)
*G01T 1/02* (2006.01)
*G01T 1/16* (2006.01)
*G01T 1/161* (2006.01)
*G01T 1/26* (2006.01)
*G01T 1/29* (2006.01)
*H03H 9/215* (2006.01)

(52) U.S. Cl.
CPC .................. *G01T 1/16* (2013.01); *G01T 1/26* (2013.01); *H03H 9/215* (2013.01); *G01N 2223/102* (2013.01)

(58) Field of Classification Search
CPC ....... G01N 2223/102; G01T 1/02; G01T 1/16; G01T 1/1606; G01T 1/161; G01T 1/202; G01T 1/2023; G01T 1/29; G01T 1/26; A61B 6/037; A61B 6/42; A61B 6/4208; A61B 6/4258
See application file for complete search history.

(56) References Cited

U.S. PATENT DOCUMENTS

| | | | |
|---|---|---|---|
| 3,094,615 A * | 6/1963 | Rose ......................... | G01T 1/29 250/336.1 |
| 3,207,982 A * | 9/1965 | Rose ......................... | G01T 1/29 219/121.22 |
| 3,492,480 A * | 1/1970 | Vogel ....................... | G01T 1/29 250/281 |

OTHER PUBLICATIONS

Abdullah Alodhayb, Quartz tuning fork, a low-cost orthogonal measurement tool for the characterization of low-vol. liquid reagents, Measurement 152 (2020), 107313. (Year: 2020).*
Fourien, "Quester Q10", Company Website, First available online Jul. 2, 2020.
Nadyah Alanazi, et al., "Quartz Tuning Fork Sensor-Based Dosimetry for Sensitive Detection of Gamma Radiation", Materials 2021, 14, 7035, pp. 1-10, First available online Nov. 19, 2021.
Abdullah Alodhayb, "Quartz tuning fork, a low-cost orthogonal measurement tool for the characterization of low-vol. liquid reagents", Measurement, vol. 152 (2020), 107313, pp. 1-6, First available online Nov. 27, 2019.

* cited by examiner

SENSITIVE DETECTION OF LOW DOSES OF BETA PARTICLES USING QUARTZ CRYSTAL OSCILLATORS

FIELD AND BACKGROUND

The disclosure of the present application relates to a system, and particularly to a system and a method for determining beta radiation intensity based on at least one calculated resonance frequency value and at least one calculated quality factor.

DESCRIPTION OF RELATED ART

Beta particles originate from unstable nucleuses during radioactive decay processes. So, beta plus and beta minus can be emitted when either one proton is converted into a neutron or one neutron is converted into a proton inside the unstable nucleus, respectively. These two types of emissions are beneficial in many fields such as medicine, research, and industry.

In medicine, particularly in cancer diagnosis, positron emission tomography (PET) takes advantage of the annihilation process of beta plus particles, which is the main mechanism of forming an image of clustered radiation inside tumors. Beta minus is commonly used in Brachytherapy and bone cancer for treatment, in which a beta source is inserted near the tumor region to exploit the full energy transfer and to avoid particle range issues.

In industry on the other hand, beta minus has many applications such as thine material thickness measurement and food safety and quality.

The growing utilization of radioactive sources in a wide range of these and other applications has significantly increased the demand for inexpensive, accurate, and portable devices for the detection of nuclear radiation. One of the fundamental principles of radiation protection is that exposure should be as low as reasonably achievable because exposure to nuclear radiation is hazardous to human life. It can cause cellular destruction, leading to DNA damage and cancer, particularly in cases of excess exposure.

Although there are existing methods for detecting nuclear radiation with high accuracy, there is a need for a sensitive, cost-efficient, and small-size means of detecting nuclear radiation. Thus, a system and a method using the same for solving the aforementioned problems are desired.

SUMMARY

The present subject matter relates to a system which, in one embodiment, includes an electrical sensor including at least one prong and a cylindrical substrate. The at least one prong can include a first section and a second section. The first section can include a plurality of planar surfaces. Each of the plurality of planar surfaces can have a first end and a second end. The first end of each of the plurality of planar surfaces can be connected to a cylindrical substrate. The second end of each of the plurality of planar surfaces can be connected to the second section, wherein each of the plurality of planar surfaces can include a first material. One of the plurality of planar surfaces can be coated with a second material to form a first composite material, and wherein the first composite material can be different from a material of the second section. A beta radiation source can be configured to irradiate the first composite material of the one of the plurality of planar surfaces and the material of the second section with beta radiation. An impedance analyzer can be configured to measure at least one impedance value from the electrical sensor. A data acquisition device can be configured to calculate at least one resonance frequency value based on the measured at least one impedance value. The data acquisition device can also be configured to calculate at least one quality factor value based on the calculated at least one resonance frequency value.

In an embodiment, the electrical sensor can be a quartz tuning fork.

In another embodiment, the first material and the second material can be quartz and silver, respectively.

In an additional embodiment, the material of the second section can be the first material.

In a supplementary embodiment, the material of the second section can be the first material which is coated with a third material to form a second composite material.

In an embodiment, the third material can be an aluminum film.

In another embodiment, the beta radiation source can be a strontium-90 beta radiation source.

In a further embodiment, the present subject matter relates to a method of determining an intensity of beta radiation based on a calculated resonance frequency and a calculated quality factor, wherein the method includes using the system as described herein to irradiate the first composite material of the one of the plurality of planar surfaces and the material of the second section with beta radiation from the beta radiation source. The method can further include measuring at least one impedance value from the electrical sensor with the impedance analyzer, calculating at least one resonance frequency value based on the measured at least one impedance value, calculating at least one quality factor value based on the calculated at least one resonance frequency value, and determining the intensity of beta radiation based on the calculated at least one resonance frequency value and the calculated at least one quality factor value.

In a non-limiting embodiment, the at least one resonance frequency value can have a range of about 32.9567 kHz to about 32.9922 kHz. In another non-limiting embodiment, the at least one resonance frequency value can have a range of about 32.9567 kHz to about 33.0162 kHz.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
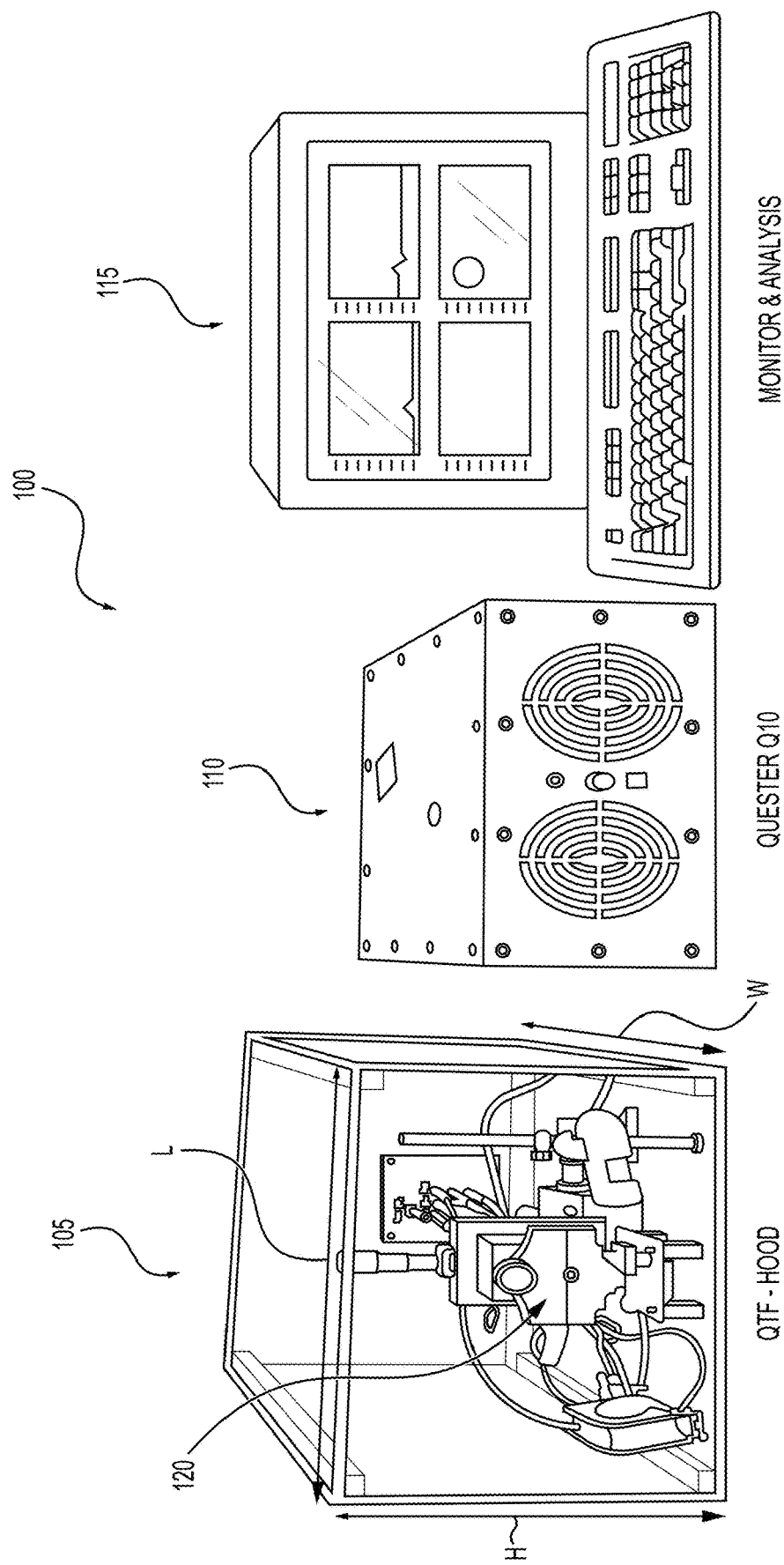
FIG. 1 is a perspective view of an overall system of the present subject matter.

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Figure 2:
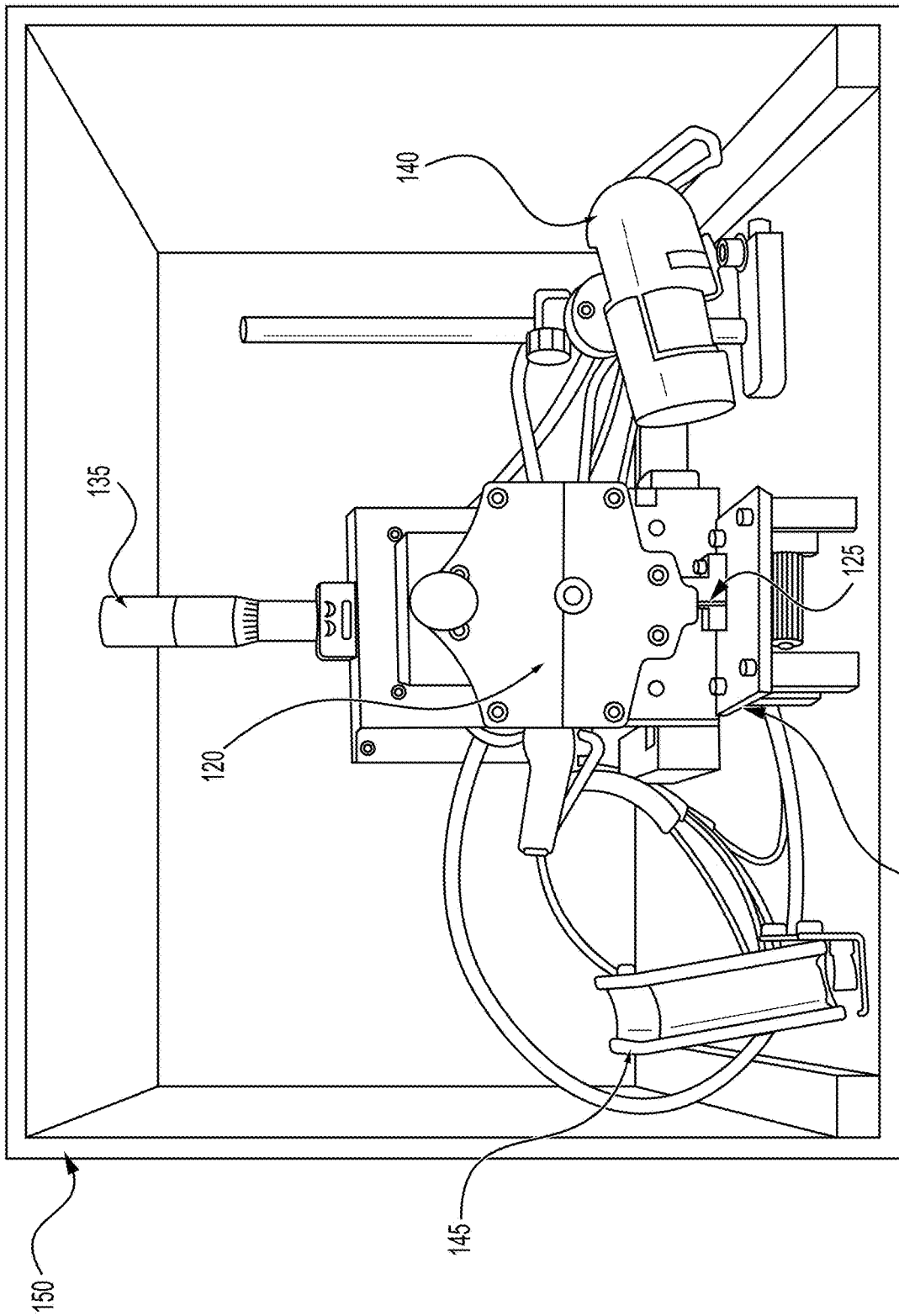
FIG. 2 is a quartz tuning fork (QTF) subsystem of the system of FIG. 1.

FIG. 1 depicts, in an embodiment, an overall system (100) having a quartz tuning fork (QTF) subsystem (105), a main controller unit (110), and a data acquisition device (115). As shown in FIGS. 1-2, the QTF subsystem (105) can include a QTF holder (120), an electrical sensor (125), a sample stage (130), a vernier caliper (135), a camera (140), and a cooling fan (145) which are all enclosed within a QTF hood (150). The QTF hood (150) can protect the electrical sensor (125) from air pollution and vibration. In an embodiment, the QTF hood (150) can have a dimension of about 36.5 cm in length (L), about 24.5 cm in height (H), and about 34.4 cm in width (W) as shown in FIGS. 1-2. The QTF holder (120) can be configured to hold the electrical sensor (125) in a vertical position.

As a non-limiting example, the electrical sensor (125) can be a quartz tuning fork (QTF). The camera (140) can be configured to capture the position of the electrical sensor (125) to ensure that it is properly connected to the QTF holder (120). The cooling fan (145) can be configured to control heat generated within the QTF hood (150). The vernier caliper (135), which can be attached to the QTF holder (120), can be configured to move the electrical sensor (125) vertically to adjust the distance between the electrical sensor (125) and the sample stage (130). In another non-limiting embodiment, the distance can be set at about 1.9 cm. The sample stage (130) can be configured to hold analyte sample(s). In a further embodiment, the analyte sample(s) can be a water droplet.

The data acquisition device (115), which can be a personal computer (PC) as shown in FIG. 1, among other potential data acquisition devices (115), can display the position of the electrical sensor (125) via the camera (140) and can have a customized Python program installed therein. The data acquisition device (115) can be configured to calculate at least one resonance frequency value based on a measured at least one impedance value as described herein; and can be configured to calculate at least one quality factor value based on the calculated at least one resonance frequency value.

Such calculations can be conducted using procedures described in full in the Examples presented herein.

Figure 3:
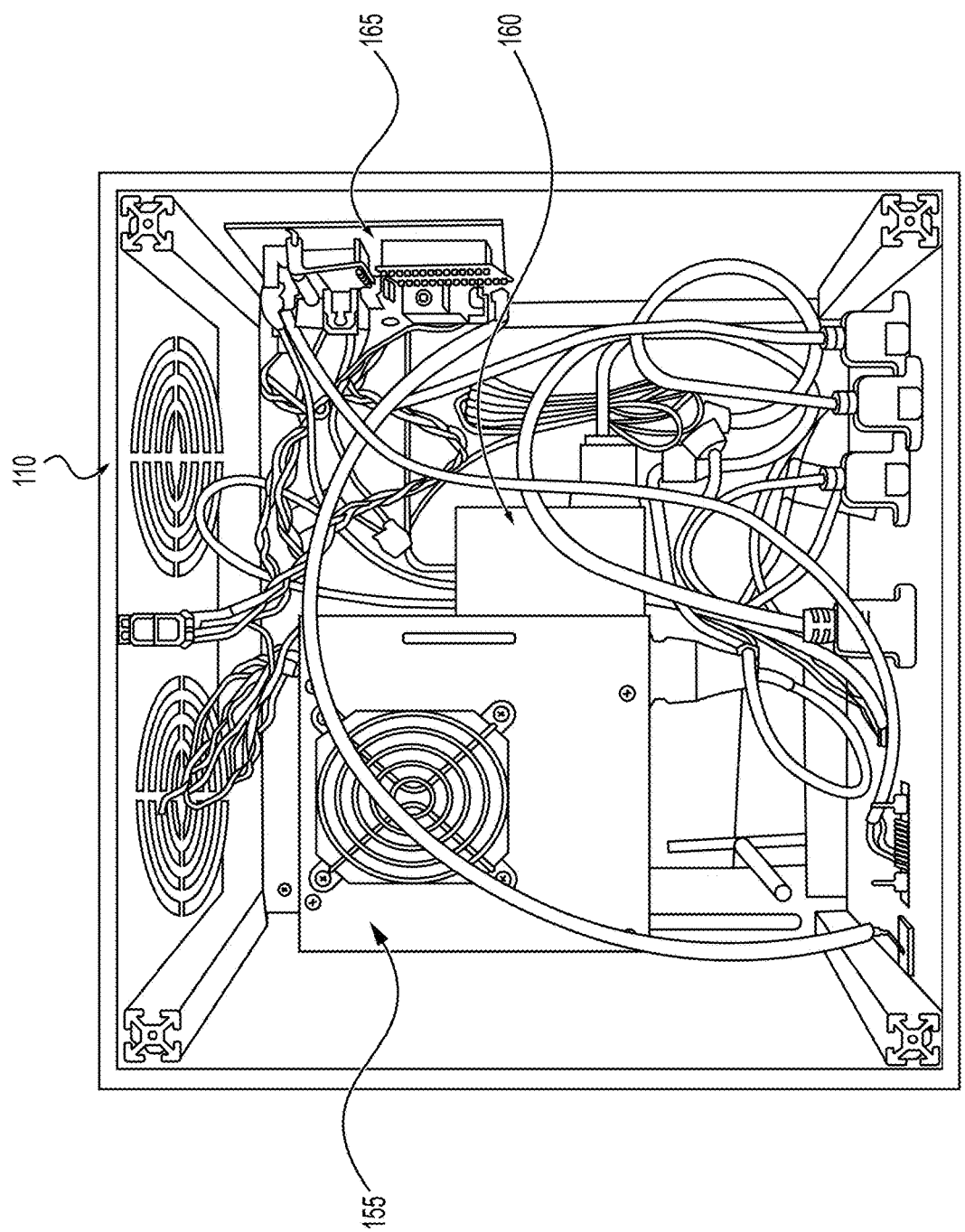
FIG. 3 is a main controller unit of the system of FIG. 1.
Figure 4:
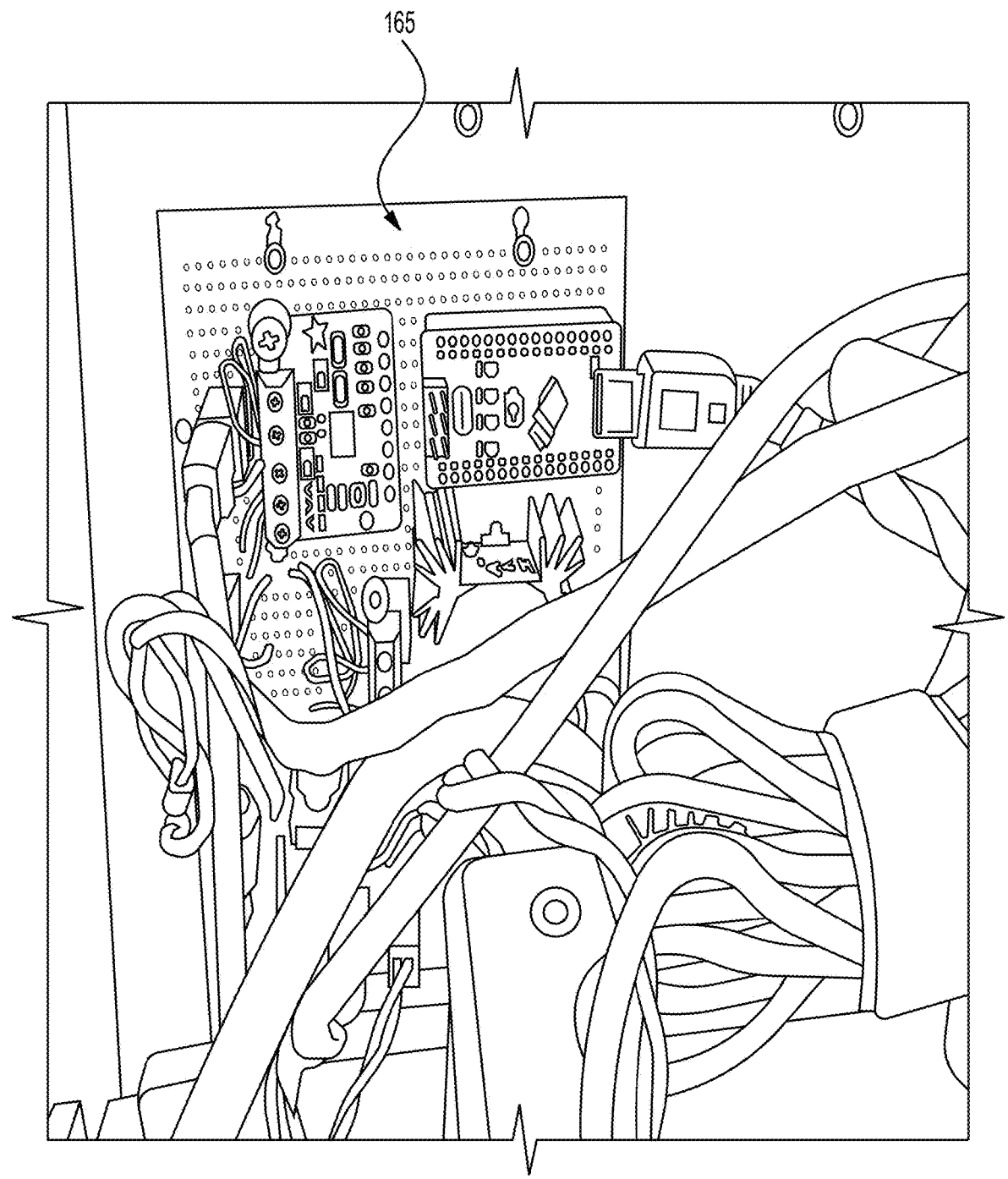
FIG. 4 is a close-up view of an AC/DC circuit board within the main controller of FIG. 1.

Within the main controller unit (110), there can be a power supply (155), a Celeron® central processing unit (CPU) (160), and an AC/DC circuit board (165), as shown in FIGS. 3-4. In certain non-limiting embodiments, the Celeron® CPU (160) can be an Intel® Celeron® Processor N3050 @ 1.60 GHz. The power supply (155) can provide power to at least the Celeron® CPU (160) and the AC/DC circuit board (165). The AC/DC circuit board (165) can include an impedance analyzer (170) configured to measure at least one impedance value from the electrical sensor (125) as shown in FIG. 5.

Figure 5:
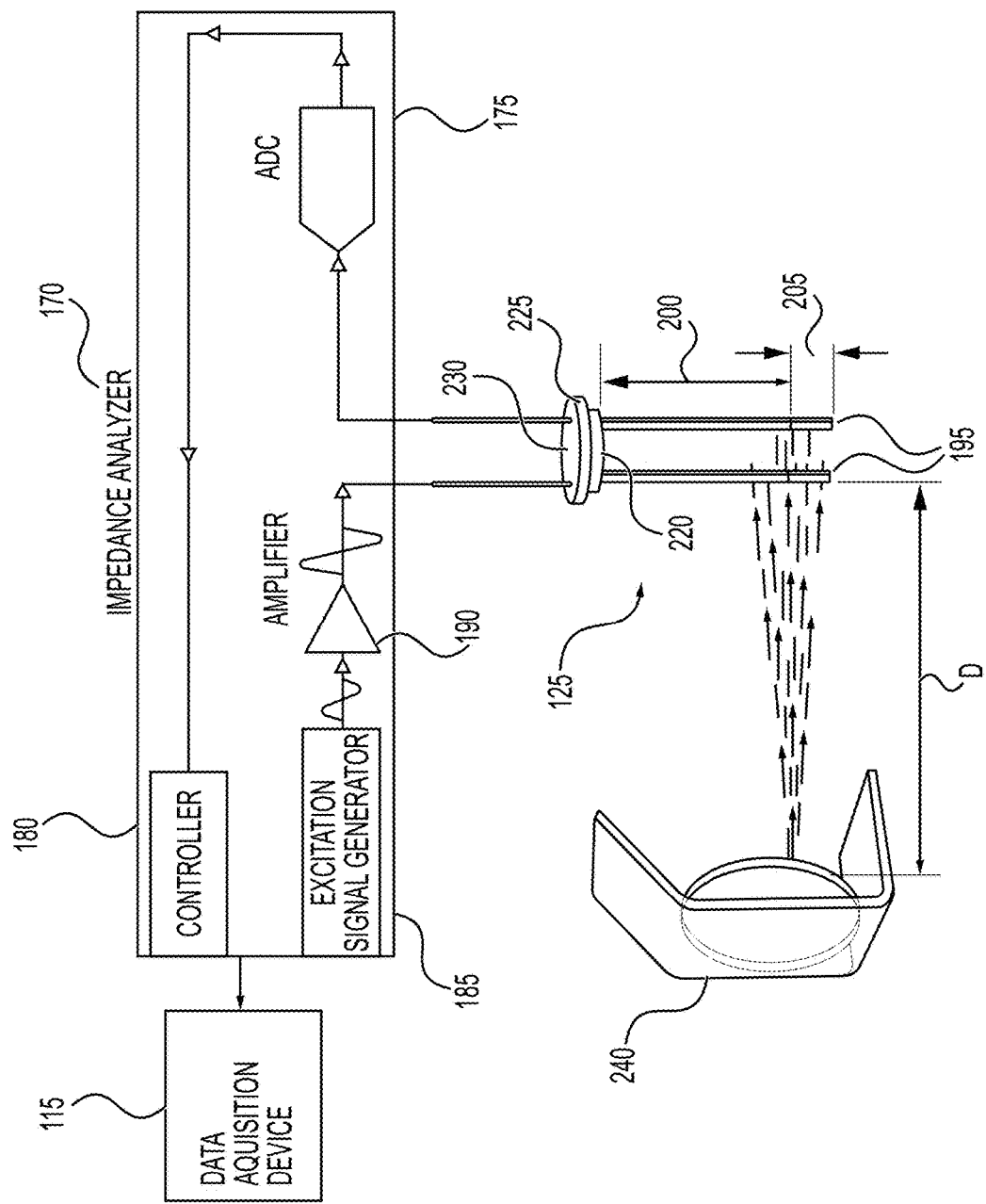
FIG. 5 is a block diagram of the system of FIG. 1.
Figure 6:
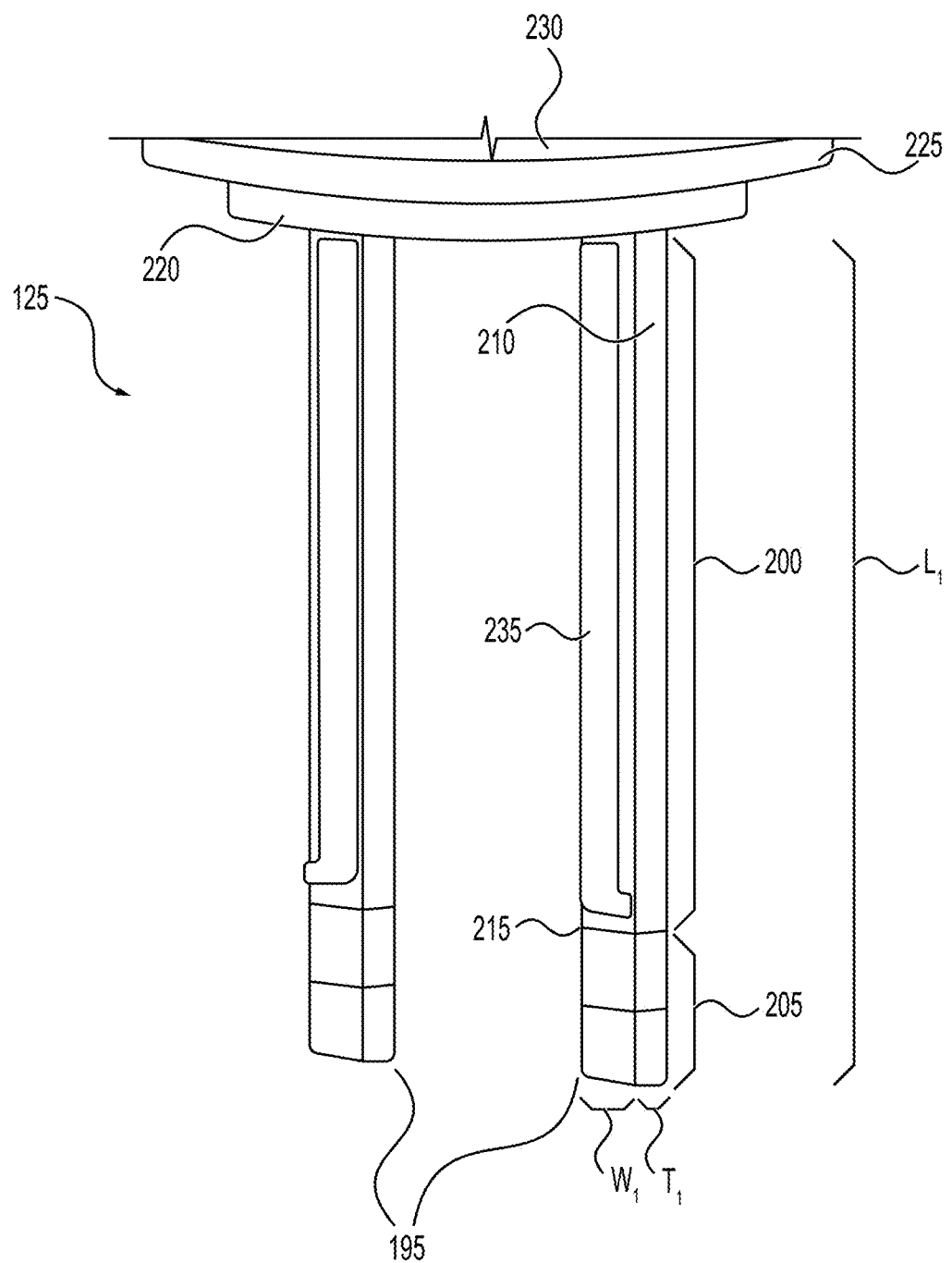
FIG. 6 is a close-up view of a QTF sensor of the system of FIG. 5.

In FIG. 5, the impedance analyzer (170) can include an analog-to-digital converter (ADC) (175), a controller (180), an excitation signal generator (185), and an amplifier (190). As shown in FIGS. 5-6, the electrical sensor (125) can include at least one prong (195). As a non-limiting example, the at least one prong (195) can include two prongs as shown in FIGS. 5-6. As another non-limiting example, the at least one prong (195) can have a dimension of about 3.73 mm in length (L1), about 0.52 mm in width (W1), and about 0.3 mm in thickness (T1).

The at least one prong (195) can have a first section (200) and a second section (205). The first section (200) and the second section (205) can each have a plurality of planar surfaces. Each of the plurality of planar surfaces of the first section (200) can have a first end (210) and a second end (215). The first end (210) of each of the plurality of planar surfaces can be connected to a second surface (220) of a substrate (225) of the electrical sensor (125), as shown in FIGS. 5-6.

In a non-limiting embodiment, the substrate (225) can have a cylindrical shape, although other shapes can be used without departing from the scope of the present subject matter. As shown in FIGS. 5-6, the ADC (175) and the amplifier (190) can be in communication with the electrical sensor (125) via a first end (230) of the substrate (225). The second end (215) of each of the plurality of planar surfaces of the first section (200) can be connected to the second section (205) of the electrical sensor (125). Each of the plurality of planar surfaces of the first section (200) and the second section (205) can have a first material.

In a first embodiment of the electrical sensor (125) as shown in FIGS. 5-6, one of the plurality of planar surfaces of the first section (200) can be coated with a second material (235) to form a first composite material such that the first composite material is different from the first material of the second section (205) as shown in FIGS. 5-6. In another non-limiting embodiment, the one of the plurality of planar surfaces of the first section (200) can be substantially or entirely coated with the second material (235). It should be understood that "substantially coated" in this regard means that more than about ½ or more than about ¾ of the one of the plurality of planar surfaces of the first section (200) is coated with the second material (235) as shown in FIGS. 5-6.

In a further non-limiting embodiment, the first material and the second material can be quartz and silver, respectively. In certain non-limiting embodiments, the silver can be a silver piezoelectric electrode configured to drive the at least one prong (195). Hereinafter, the electrical sensor (125) in the first embodiment having the combination of the first composite material with the silver piezoelectric electrode on the first section (200) and the quartz on the second section (205) will be referred to as "QTF sensor (125)".

In a second embodiment of the electrical sensor (125) as shown in FIGS. 5-6, the first material, which can be quartz as mentioned above, of the second section (205) can be coated with a third material to form a second composite material while the one of the plurality of planar surfaces of the first section (200) can be the mentioned first composite material. In a particular non-limiting embodiment, the third material can be a thin layer of aluminum (Al) with a thickness of about 40 nm. Hereinafter, the electrical sensor (125) in the second embodiment having the combination of the first composite material with the silver piezoelectric electrode on the first section (200) and the second composite material with the thin layer of aluminum on the second section (205) will be referred to as "Al-coated QTF sensor (125)".

A beta radiation source (240), which can be located on the sample stage (130) and at a side of the electrical sensor (125), can be configured to irradiate the first composite material of the one of the plurality of planar surfaces and the material of the second section (205) with beta radiation as shown in FIGS. 2 and 5. While FIG. 5 shows the beta radiation source (240) located on the left side of the electrical sensor (125), it should be understood that the location of the beta radiation source (240) can be on any of the sides with respect to the electrical sensor (125) without departing from the scopes of the present subject matter. As a non-limiting example, a distance (D) between the radiation source (240) and the electrical sensor (125) can be about 1.5 cm. As another non-limiting example, the beta radiation source (240) can be a strontium-90 (Sr-90) isotope with an activity of about 0.1 uCi and a half-life of about 28.6 years.

In a further embodiment, the present subject matter relates to a method of determining an intensity of beta radiation based on a calculated resonance frequency and a calculated quality factor which can include providing the system (100) above to conduct irradiating of the first composite material of the one of the plurality of planar surfaces and the material of the second section (205) with beta radiation from the beta radiation source (240); measuring at least one impedance value from the electrical sensor (125) with the impedance analyzer (170); calculating at least one resonance frequency value based on the measured at least one impedance value; calculating at least one quality factor value based on the calculated at least one resonance frequency value; and determining the intensity of beta radiation based on the calculated at least one resonance frequency value and the calculated at least one quality factor value.

In a non-limiting embodiment, the at least one resonance frequency value can have a range of about 32.9567 kHz to about 32.9922 kHz. In another non-limiting embodiment, the at least one resonance frequency value can have a range of about 32.9567 kHz to about 33.0162 kHz.

The following examples illustrate the present teachings.

EXAMPLES

Example 1

Determining Beta Radiation Intensity for QTF Sensor (Without Al Coating)

The process of determining an intensity of beta radiation for the QTF sensor was conducted using the following steps.

Providing the QTF sensor: QTF sensor (125), which was provided, can include the first composite material with the silver piezoelectric electrode on the first section (200) and the quartz on the second section (205) as shown in FIGS. 5-6.

Figure 7:
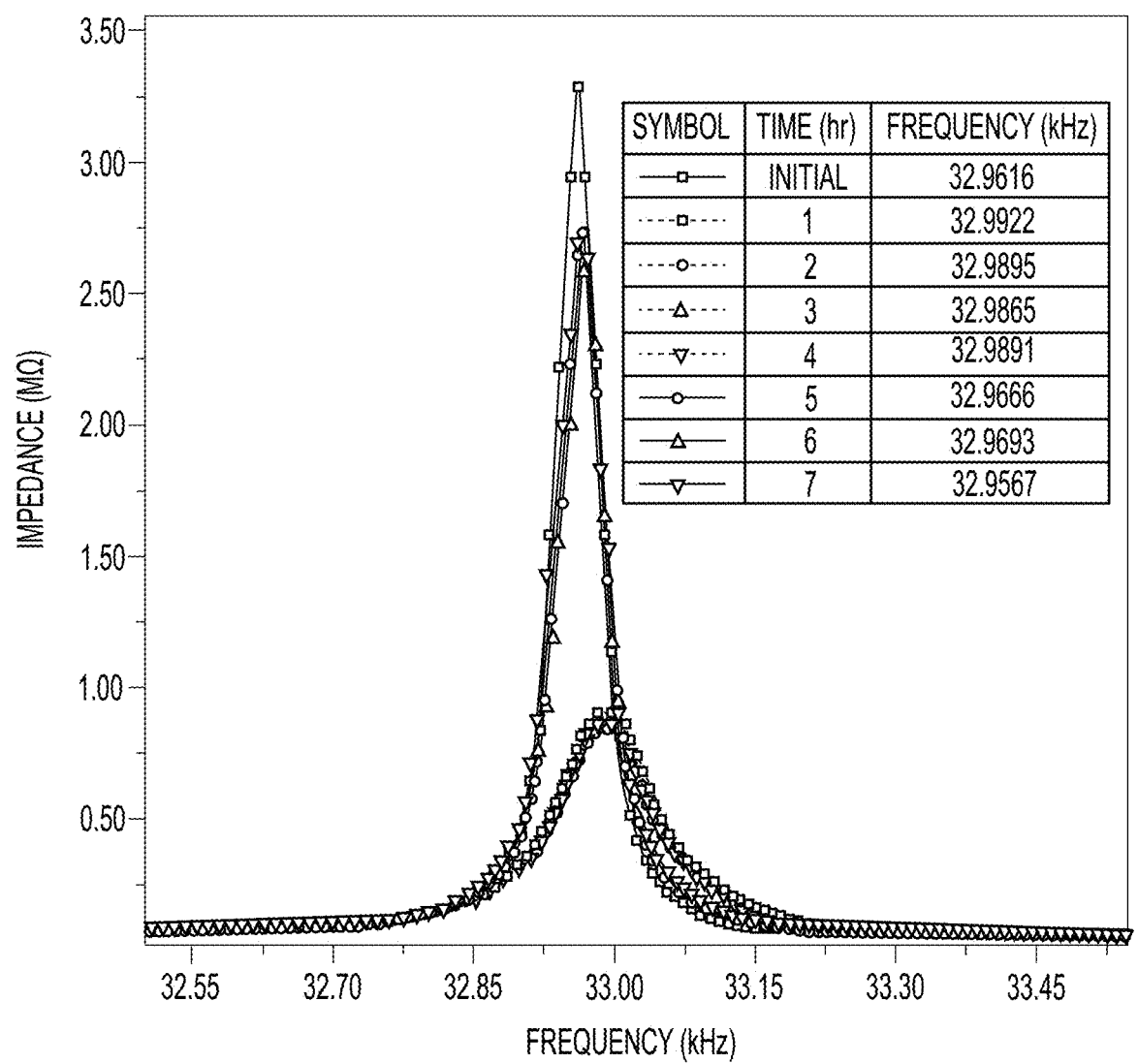
FIG. 7 depicts resonance frequency and impedance measurements for the QTF sensor.
Figure 8:
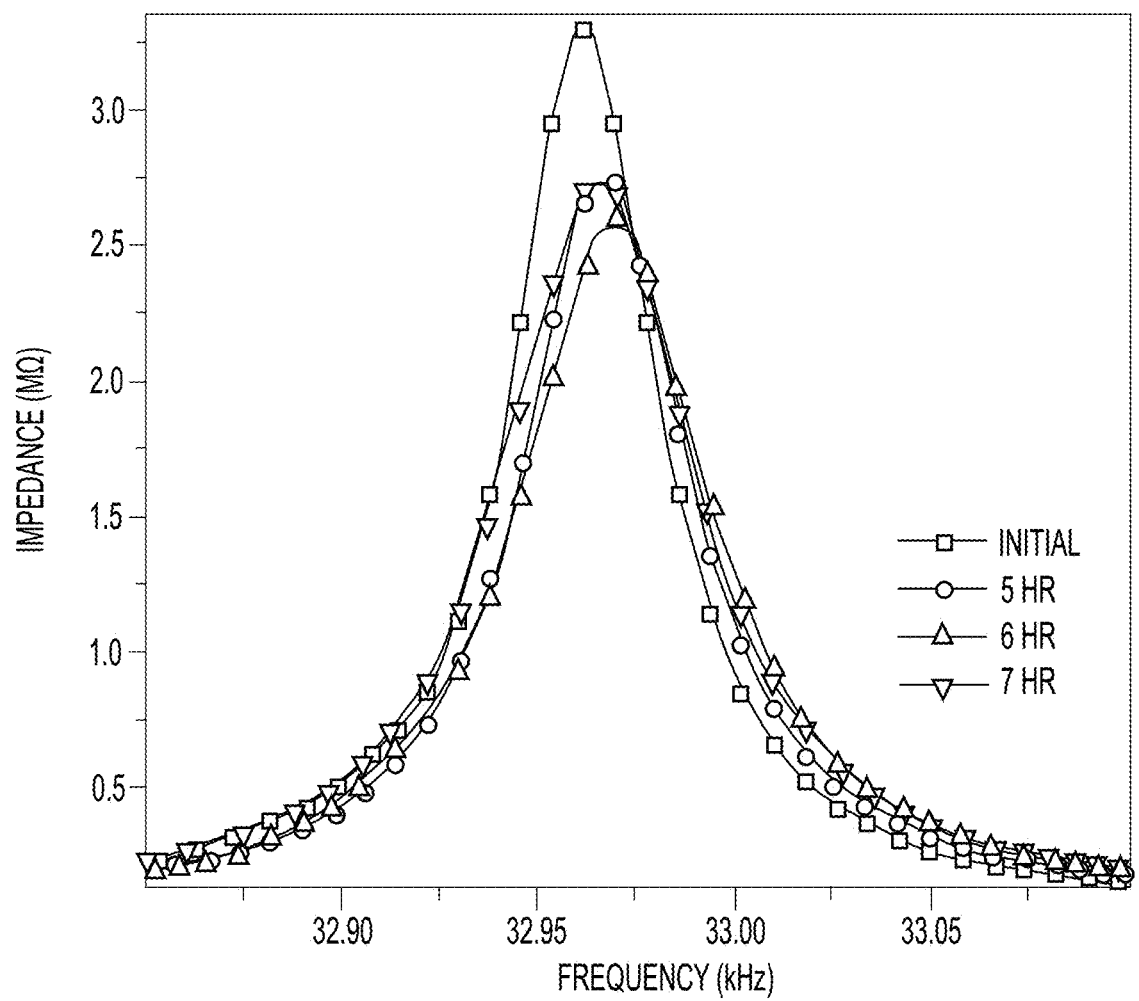
FIG. 8 depicts details of the resonance frequency change without irradiation as shown in FIG. 7.
Figure 9:
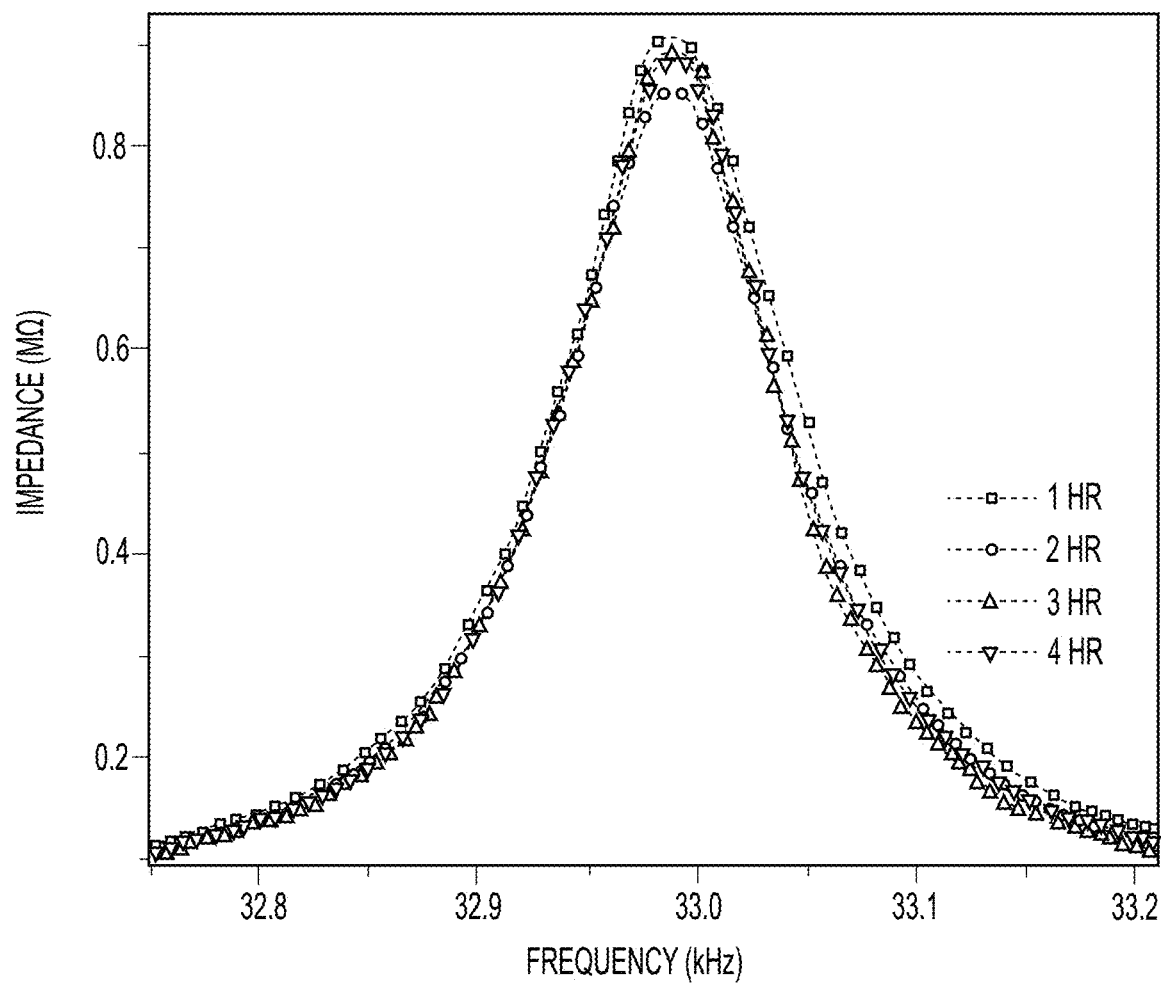
FIG. 9 depicts details of the resonance frequency change with irradiation as shown in FIG. 7.

Irradiation and Measuring: The first composite material with the silver piezoelectric electrode on the first section (200) and the quartz on the second section (205) were not initially (i.e., 0 hr.) irradiated. For the next four hours (i.e., at about 1 hr., at about 2 hr., at about 3 hr., and at 4 about hr.), the first composite material with the silver piezoelectric electrode on the first section (200) and the quartz on the second section (205) were irradiated with the beta radiation from the beta radiation source (240). Subsequently, the beta radiation source (240) was turned off for the next three hours (i.e., at about 5 hr., at about 6 hr., and at about 7 hr.). Throughout the seven hours, including at 0 hr., the impedance values from the QTF sensor (125) were measured by sweeping a frequency across the resonance and recording the impedance's absolute value using the impedance analyzer (170) as shown in FIG. 5. The results of the measurements are shown in FIGS. 7-9. Close up details of the resonance frequency change without irradiation as shown in FIG. 7 can be seen in FIG. 8. Likewise, close up details of the resonance frequency change with irradiation as shown in FIG. 7 can be seen in FIG. 9.

Calculation of Resonance Frequency: The measured impedance and frequency values as shown in FIGS. 7-9 were then fitted using a Lorentz function equation (see Eq. 1 below) to calculate the resonance frequency at full width half maximum (FWHM), @:

$$B = B_0 + \left(\frac{2A}{\pi}\right)\left(\frac{\omega}{4(\alpha - \alpha_c)^2 + \omega^2}\right) \quad (1)$$

wherein,
B—the impedance of the real component plotted on the y-axis;
$B_0$—is an offset;
A—is the area;
ω—is the difference between the value of the resonance frequency at the FWHM; and
a and $a_c$—are the resonance frequency at zero and the maximum amplitude of the real component.

Calculation of Quality Factor: Based on the calculated resonance frequency FWHM, ω, and the maximum amplitude of the real component, $a_c$, the quality factor can be calculated using Eq. 2 below, with the variables having the same definitions as for Eq. 1, above:

$$Q = a_c/\omega \quad (2)$$

Figure 10:
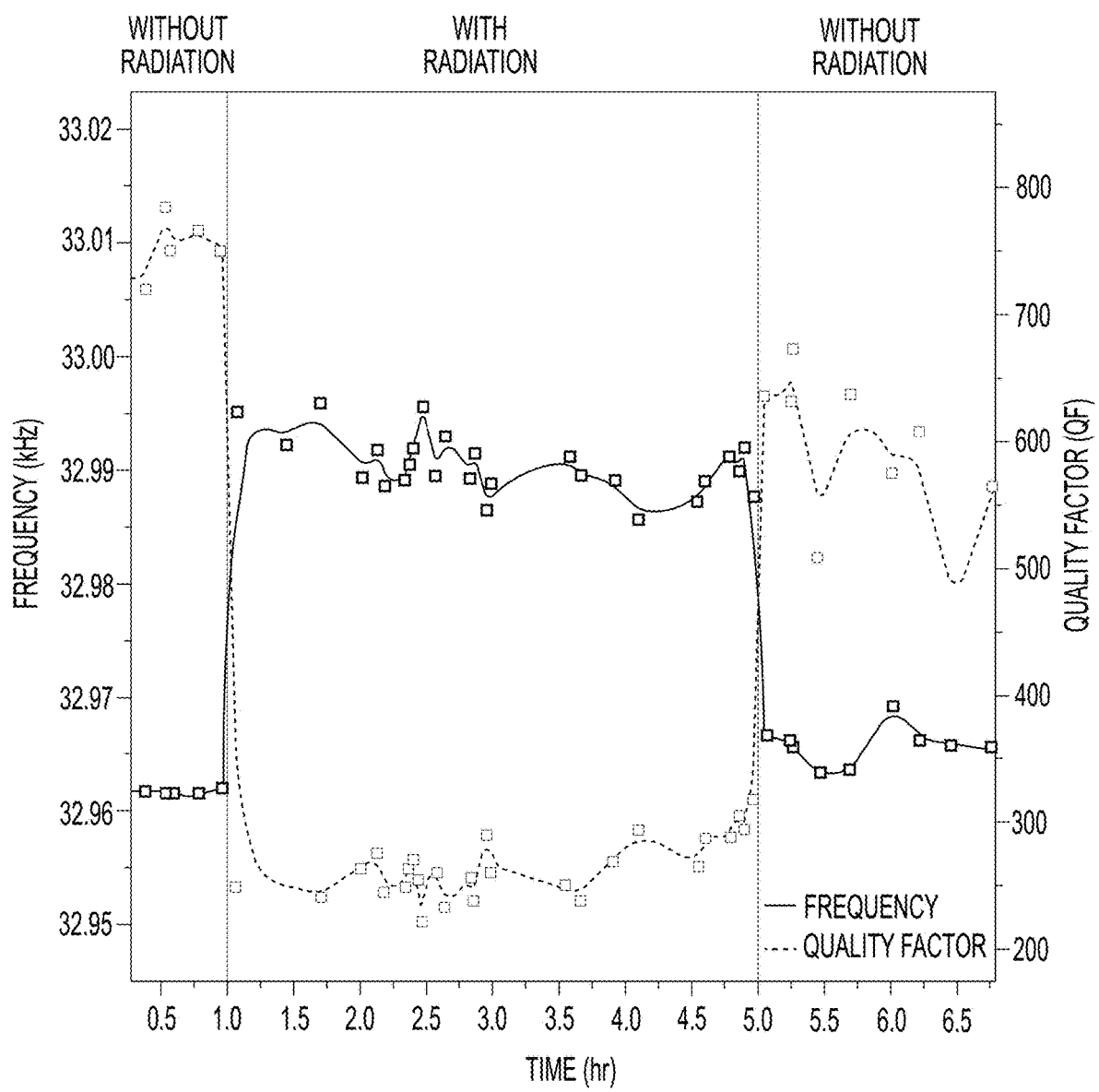
FIG. 10 depicts calculated resonance frequency and quality factor of the QFT sensor.

As shown in FIG. 10, the Lorentz function is fitted with the data of the resonance frequency response of the QTF sensor (125) to radiation as a function of time. FIG. 10 also shows the calculated quality factors as a function of time. Based on the response frequencies and the quality factors, the beta radiation intensity can be determined. As shown in FIG. 10, as the heat from the beta radiation is increased with respect to time, the silver piezoelectric electrode and the quartz of the QTF sensor (125) will undergo thermal expansion. Since the thermal expansion coefficient of silver is greater than that of quartz, the latter will suffer a tensile stress because of the silver. Accordingly, the spring constant of the whole QTF sensor (125) will increase, causing the resonance frequency to increase. After removing the beta radiation, the tensile stress from the quartz will be released, causing the resonance frequency to return back to about the same values as during the initial start (from 0 hr. to about 1 hr.) as shown in FIG. 10.

Example 2

Determining Beta Radiation Intensity for QTF Sensor (Al Coating)

The process of determining an intensity of beta radiation for an Al-coated QTF sensor was conducted using the following steps.

Providing the QTF sensor: Al-coated QTF sensor (125), which was provided, can include the first composite material with the silver piezoelectric electrode on the first section (200) and the second composite material with Al layer on the second section (205) as shown in FIGS. 5-6.

Figure 11:
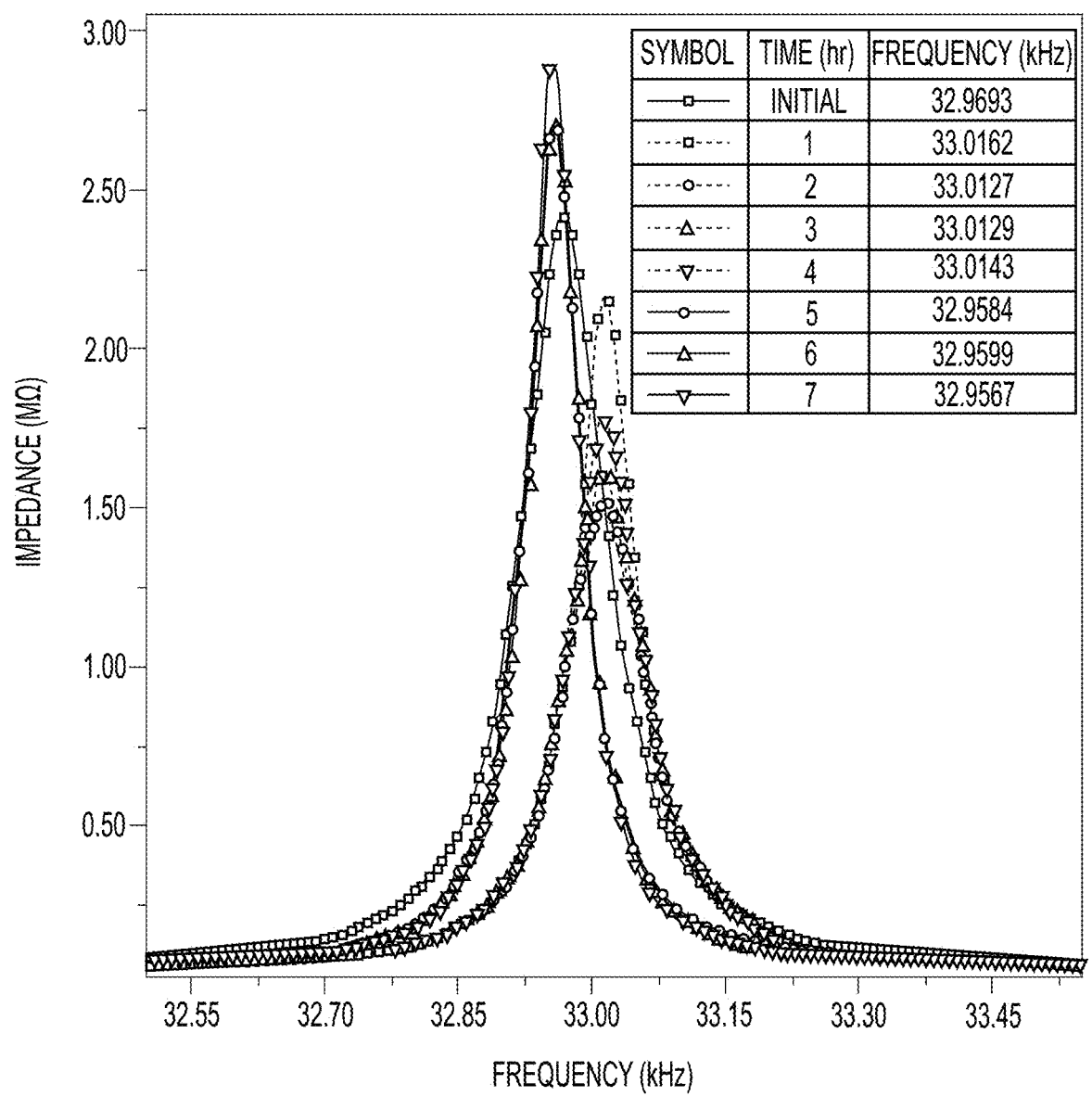
FIG. 11 depicts resonance frequency and impedance measurements for the Al-coated QTF sensor.
Figure 12:
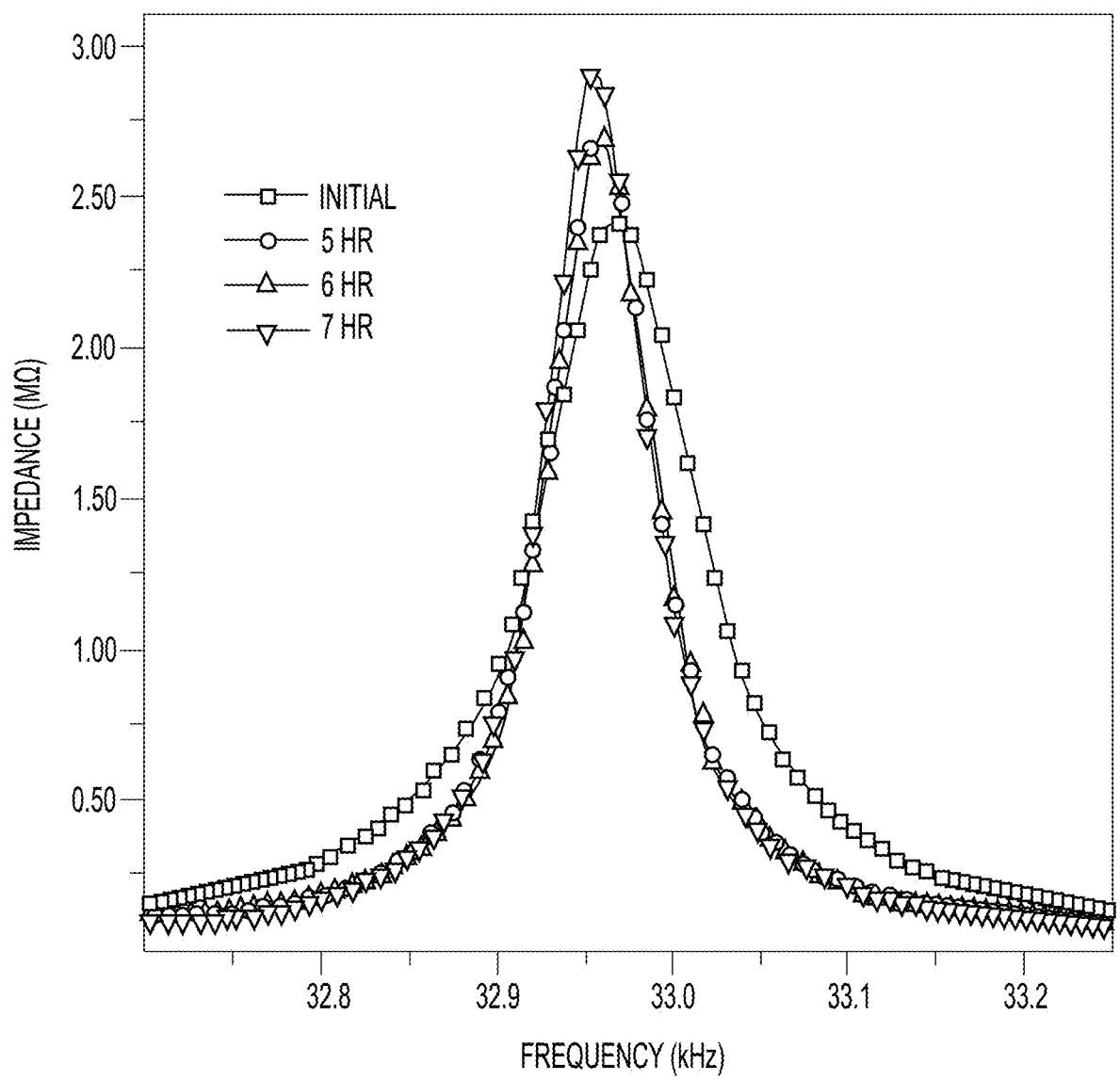
FIG. 12 depicts details of the resonance frequency change without irradiation as shown in FIG. 11.
Figure 13:
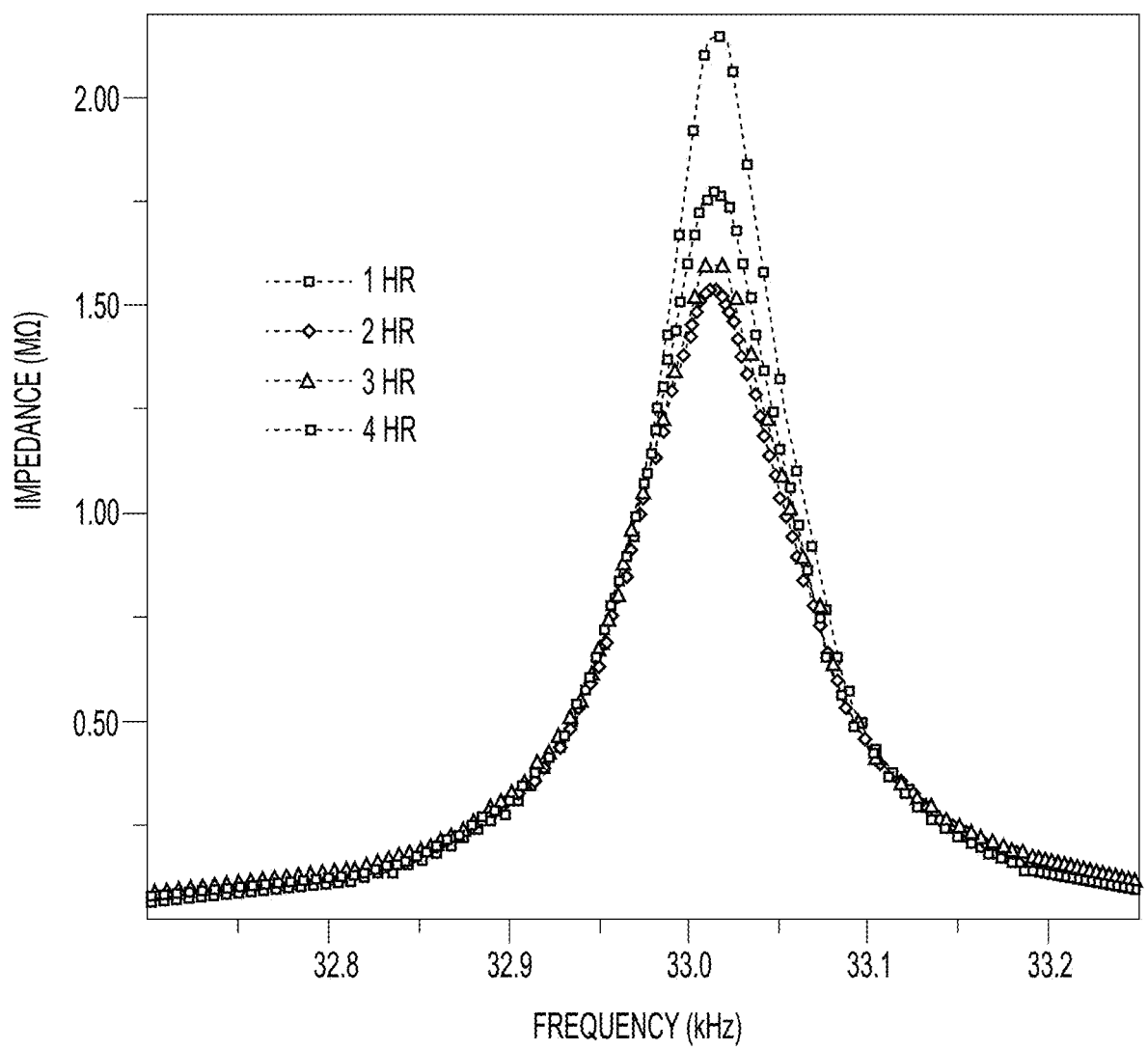
FIG. 13 depicts details of the resonance frequency change with irradiation as shown in FIG. 11.

Irradiation and Measuring: The first composite material with the silver piezoelectric electrode on the first section (200) and the second composite material with Al layer on the second section (205) were not initially (i.e., 0 hr.) irradiated. For the next four hours (i.e., at about 1 hr., at about 2 hr., at about 3 hr., and at 4 about hr.), the first composite material with the silver piezoelectric electrode on the first section (200) and the second composite material with Al layer on the second section (205) were irradiated with the beta radiation from the beta radiation source (240). Subsequently, the beta radiation source (240) was turned off for the next three hours (i.e., at about 5 hr., at about 6 hr., and at about 7 hr.). Throughout the seven hours including at 0 hr., the impedance values from the Al-coated QTF sensor (125) were measured by sweeping a frequency across the resonance and recording the impedance's absolute value using the impedance analyzer (170) as shown in FIG. 5. The results of the measurements are shown in FIGS. 11-13. Close up details of the resonance frequency change without irradiation as shown in FIG. 11 can be seen in FIG. 12. Likewise, close up details of the resonance frequency change with irradiation as shown in FIG. 11 can be seen in FIG. 13.

Calculation of Resonance Frequency: The measured impedance and frequency values as shown in FIGS. 11-13 were then fitted using a Lorentz function equation (see Eq. 1 below) to calculate the resonance frequency at full width half maximum (FWHM), ω:

$$B = B_0 + \left(\frac{2A}{\pi}\right)\left(\frac{\omega}{4(\alpha - \alpha_c)^2 + \omega^2}\right) \quad (1)$$

wherein,
B—the impedance of the real component plotted on the y-axis;
$B_0$—is an offset;
A—is the area;
ω—is the difference between the value of the resonance frequency at the FWHM; and
a and $a_c$—are the resonance frequency at zero and the maximum amplitude of the real component.

Calculation of Quality Factor: Based on the calculated resonance frequency FWHM, ω, and the maximum amplitude of the real component, $a_c$, the quality factor can be calculated using Eq. 2 below, with the variables having the same definitions as for Eq. 1, above:

$$Q = a_c/\omega \quad (2)$$

Figure 14:
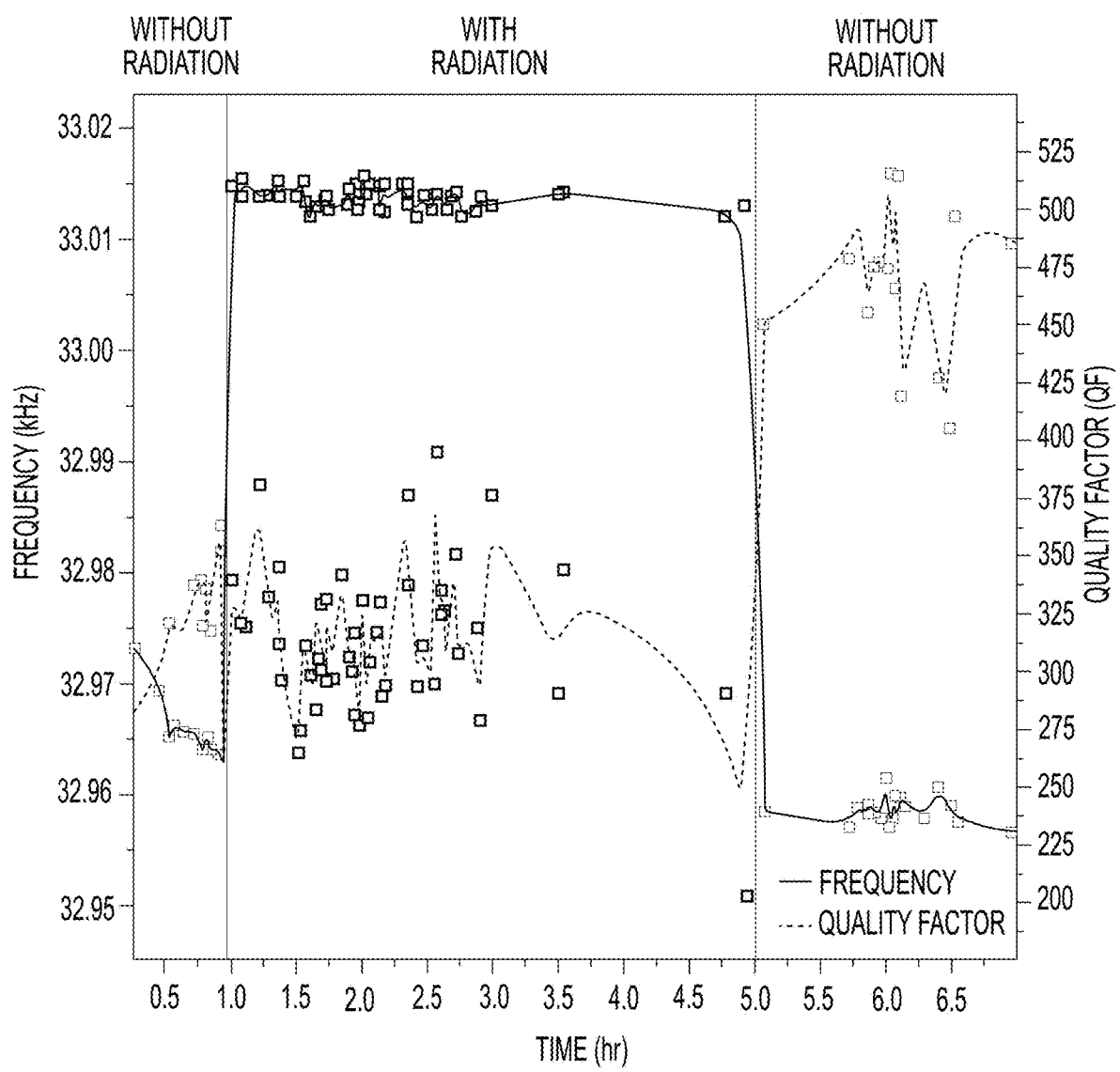
FIG. 14 depicts calculated resonance frequency and quality factor for the Al-coated QFT sensor.

As shown in FIG. 14, the Lorentz function is fitted with the data of the resonance frequency response of the Al-coated QTF sensor (125) to radiation as a function of time. FIG. 14 also shows the calculated quality factors as a function of time. Based on the response frequencies and the quality factors, the beta radiation intensity can be determined. As shown in FIG. 14, as the heat from the beta radiation is increased with respect to time, the silver piezoelectric electrode and the second composite material with Al layer on the second section (205) of the Al-coated QTF sensor (125) will undergo thermal expansion. Since the thermal expansion coefficient of silver is greater than that of quartz, the latter will suffer a tensile stress because of the silver. Accordingly, the spring constant of the whole Al-coated QTF sensor (125) will increase, causing the resonance frequency to increase. After removing the beta radiation, the tensile stress from the quartz will be released causing the resonance frequency to return back to about the same values as during the initial start (from 0 hr. to about 1 hr.) as shown in FIG. 14.

Compared to the resonance frequency of the QTF sensor (125) as shown in FIG. 10, the resonance frequency of the Al-coated QTF sensor (125) is higher as shown in FIG. 14. This is because the aluminum coating is covering more area on the QTF prongs (195), thereby causing more tensile stress as a result of thermal heating by the beta radiation.

It is to be understood that the system, the quartz tuning fork, and the method of determining beta radiation intensity based on calculated resonance frequency and calculated quality factor are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A system comprising:
an electrical sensor comprising at least one prong and a cylindrical substrate, the at least one prong comprising a first section and a second section, the first section comprising a plurality of planar surfaces, each of the plurality of planar surfaces having a first end and a second end, the first end of each of the plurality of planar surfaces being connected to the cylindrical substrate, and the second end of each of the plurality of planar surfaces being connected to the second section, wherein each of the plurality of planar surfaces comprises a first material, one of the plurality of planar surfaces is coated with a second material to form a first composite material, and wherein the first composite material is different from a material of the second section;
a beta radiation source configured to irradiate the first composite material of the one of the plurality of planar surfaces and the material of the second section with beta radiation;
an impedance analyzer configured to measure at least one impedance value from the electrical sensor; and
a data acquisition device configured to:
calculate at least one resonance frequency value based on the measured at least one impedance value; and
calculate at least one quality factor value based on the calculated at least one resonance frequency value.

2. The system of claim 1, wherein the electrical sensor comprises a quartz tuning fork.

3. The system of claim 1, wherein the first material and the second material comprise quartz and silver, respectively.

4. The system of claim 1, wherein the material of the second section comprises the first material.

5. The system of claim 1, wherein the material of the second section comprises the first material, which is coated with a third material to form a second composite material.

6. The system of claim 5, wherein the third material comprises an aluminum film.

7. The system of claim 1, wherein the beta radiation source comprises a strontium-90 beta radiation source.

8. A method of determining an intensity of beta radiation based on a calculated resonance frequency and a calculated quality factor comprising:
providing an electrical sensor comprising at least one prong and a cylindrical substrate, the at least one prong comprising a first section and a second section, the first section comprising a plurality of planar surfaces, each of the plurality of planar surfaces having a first end and a second end, the first end of each of the plurality of planar surfaces being connected to the cylindrical substrate, and the second end of each of the plurality of planar surfaces being connected to the second section, wherein each of the plurality of planar surfaces comprises a first material, one of the plurality of planar surfaces is coated with a second material to form a first composite material, and wherein the first composite material is different from a material of the second section;
irradiating the first composite material of the one of the plurality of planar surfaces and the material of the second section with beta radiation from a beta radiation source;
measuring at least one impedance value from the electrical sensor with an impedance analyzer;
calculating at least one resonance frequency value based on the measured at least one impedance value;
calculating at least one quality factor value based on the calculated at least one resonance frequency value; and
determining the intensity of beta radiation based on the calculated at least one resonance frequency value and the calculated at least one quality factor value.

9. The method of claim 8, wherein the first material and the second material comprise quartz and silver, respectively.

10. The method of claim 8, wherein the material of the second section comprises the first material.

11. The method of claim 10, wherein the at least one resonance frequency value comprises a range of about 32.9567 kHz to about 32.9922 kHz.

12. The method of claim 8, wherein the material of the second section comprises the first material, which is coated with a third material to form a second composite material.

13. The method of claim 12, wherein the third material comprises an aluminum film.

14. The method of claim 13, wherein the at least one resonance frequency value comprises a range of about 32.9567 kHz to about 33.0162 kHz.

15. The method of claim 8, wherein the beta radiation source comprises a strontium-90 beta radiation source.

* * * * *